United States Patent [19]

Bridger et al.

[11] 4,076,639
[45] Feb. 28, 1978

[54] LUBRICANT COMPOSITIONS

[75] Inventors: Robert F. Bridger, Hopewell; Ronald J. Cier, East Windsor, both of N.J.

[73] Assignee: Mobil Oil Corporation, New York, N.Y.

[21] Appl. No.: 718,699

[22] Filed: Aug. 30, 1976

[51] Int. Cl.$^2$ .................. C10M 1/38; C10M 3/32; C07C 153/00; C07C 154/00
[52] U.S. Cl. .................. 252/47.5; 260/455 A; 252/77
[58] Field of Search .............. 252/47.5, 48.6, 77; 260/455 A

[56] References Cited

U.S. PATENT DOCUMENTS

| 2,216,751 | 10/1940 | Rosen | 252/48.6 |
| 2,321,575 | 6/1943 | Clayton et al. | 252/48.6 |
| 2,354,550 | 7/1944 | Rosen | 252/48.6 |
| 2,601,063 | 6/1952 | Smith et al. | 252/48.6 |
| 2,897,152 | 7/1959 | Elliott et al. | 252/47.5 |
| 2,974,082 | 3/1961 | Collins | 260/455 A |
| 3,061,619 | 10/1962 | Braunwarth et al. | 252/48.6 |
| 3,314,888 | 4/1967 | Matson | 252/48.6 |
| 3,344,163 | 9/1967 | Frank et al. | 260/455 A |
| 3,833,496 | 9/1974 | Malec | 252/47.5 |

Primary Examiner—Delbert E. Gantz
Assistant Examiner—Irving Vaughn
Attorney, Agent, or Firm—Charles A. Huggett; Howard M. Flournoy

[57] ABSTRACT

Lubricant compositions are provided, comprising oils of lubricating viscosity, and greases prepared therefrom, containing a minor antiwear improving amount of an alkyl beta-thiopropionic acid ester.

18 Claims, No Drawings

LUBRICANT COMPOSITIONS

BACKGROUND OF THE INVENTION

1. Field of the Invention

This application is directed to lubricant compositions comprising oils of lubricating viscosity and greases prepared therefrom and various functional fluids such as hydraulic oils or fluids and minor amounts sufficient to improve the antiwear properties of such lubricant compositions of an alkyl betathiopropionic acid ester.

2. Description of the Prior Art

It is well known that many types of lubricant compositions particularly oils of lubricating viscosities and greases and other lubricant fluids prepared therefrom, normally exhibit poor antiwear properties during performance. Antiwear additives of the prior art have not proven completely satisfactory, particularly with respect to antiwear properties in conjunction with low corrosivity to steel, bronze and other metals. Such metals are further exemplified in a variety of industrial lubricant applications including worm gear sets (steel/bronze), table slides (steel/bronze) and hydraulic pumps (steel/brass or silver/bronze).

SUMMARY OF THE INVENTION

Lubricant media, particularly hydrocarbon oils of lubricating viscosity and greases prepared therefrom acquire improved antiwear properties when minor amounts of alkyl beta-thiopropionic acid esters are incorporated therein. More particularly, it has been found that a lubricant composition containing a major amount of an oil of lubricating viscosity or a grease prepared therefrom and a minor amount sufficient to improve the antiwear properties thereof of an alkyl beta-thiopropionic acid ester selected from the group consisting of

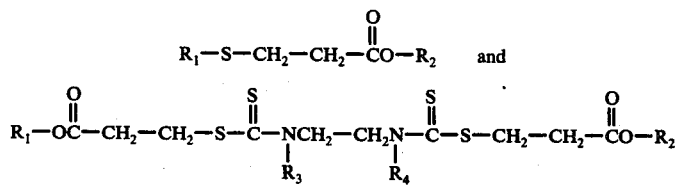

where in $R_1$ and $R_2$ are alkyl groups, straight or branched, containing from 1 to about 30 carbon atoms and $R_3$ and $R_4$ are alkyl groups, straight or branched, containing from 1 to about 12 carbon atoms provides compositions of improved antiwear properties. Especially suitable are lubricant compositions wherein $R_1$ and $R_2$, as above identified, contain from 2 to 12 carbon atoms and $R_4$ and $R_3$ contain from 1 to 6 carbon atoms.

DESCRIPTION OF SPECIFIC EMBODIMENTS

In general, the present invention is directed to lubricant compositions of the above-described types which contain a small amount sufficient to impart antiwear properties of the aforementioned sulfur-containing additives. Generally, for most applications, the additive is present in an amount from about 0.05 to about 5%, by weight of the total composition and preferably in an amount from about 0.1 to about 2% by weight. The lubricant compositions in accordance with the invention may comprise any materials that normally exhibit insufficient antiwear properties. A field of specific applicability is the improvement of liquid hydrocarbon oils boiling within the range of from about 75° F. to about 1000° F. Lubricant oils, improved in accordance with the present invention, may be of any suitable lubricating viscosity range, e.g., from about 45 SSU at 100° F to about 6,000 SSU at 100° F., and preferably, from about 50 to 250 SSU at 210° F. Thus, oils having viscosity indexes from about 70 to about 95 are preferred. The average molecular weights of such oils may range from about 250 to about 800. In general, the lubricant may comprise any mineral or synthetic oil of lubricating viscosity.

In instances where synthetic oils are desired in preference to mineral oils, they may be employed in lubricant compositions alone or in combination with mineral oils. They may also be so used as the lubricant base or vehicle for grease compositions. Typical synthetic lubricants include polyisobutylene, polybutenes, hydrogenated polydecenes, polypropylene glycol, polyethylene glycol, trimethylol propane esters, neopentyl and pentaerythritol esters, di(2-ethyl hexyl) sebacate, di(2-ethyl hexyl) adipate, dibutyl phthalate, fluorocarbons, silicate esters, silanes, esters of phosphorous-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis(p-phenoxy phenyl) ether, phenoxy phenylethers, etc.

As hereinbefore indicated, the subject thiopropionic acid ester additives may be incorporated as antiwear agents in grease compositions. Also included within the scope of this invention are various special purpose fluids, such as hydraulic oils, transmission oils, power steering oils and the like. When high temperature stability is not a requirement of the finished grease, mineral oils having a viscosity of at least 40 SSU at 100° F., and particularly those falling within the range from about 60 SSU to about 6,000 SSU at 100° F may be employed.

The lubricating vehicles of the improved greases of the present invention, containing the above-described additives, are combined with a grease-forming quantity of a thickening agent. For this purpose, a wide variety of materials can be dispersed in the lubricating vehicle in grease-forming quantities in such degree as to impart to the resulting grease composition the desired consistency. Exemplary of the thickening agents that may be employed are non-soap thickeners, such as surface-modified clays and silicas, aryl ureas, calcium complexes and similar materials. In general, grease thickeners are employed which do not melt and dissolve when used at the required temperature within a particular environment; however, in all other respects, any material which is normally employed for thickening or gelling oleaginous fluid or forming greases can be used in preparing the aforementioned improved greases in accordance with the present invention.

The subject sulfur-containing esters provide effective antiwear properties when minor amounts thereof are incorporated into various oils, greases, and functional fluids of lubricant viscosity; they are suitable for use in steel-on-steel, and steel-on-bronze applications as disclosed hereinafter. They are especially useful in steel-on-bronze applications, for example, in devices having steel and bronze worm gears.

Accordingly, a preferred embodiment of the herein disclosed invention provides a method of decreasing wear of bearing surfaces having at least two moveable parts, wherein said bearing surfaces are steel or wherein one of said bearing surfaces is steel and another of said bearing surfaces is bronze, which comprises dispersing between said surfaces a lubricant comprising an oil of lubricating viscosity characterized by the presence therein of a minor amount a lubricant composition containing a major amount of an oil of lubricating viscosity or a grease prepared therefrom and a minor amount sufficient to improve the antiwear properties thereof of an alkyl-beta-thiopropionic acid ester selected from the group consisting of:

$$R_1-S-CH_2-CH_2-\overset{O}{\underset{\|}{C}}O-R_2 \quad \text{and}$$

$$R_1-O\overset{O}{\underset{\|}{C}}-CH_2-CH_2-S-\overset{S}{\underset{\|}{C}}-\underset{\underset{R_3}{|}}{N}CH_2-CH_2\underset{\underset{R_4}{|}}{N}-\overset{S}{\underset{\|}{C}}-S-CH_2-CH_2-\overset{O}{\underset{\|}{C}}O-R_2$$

wherein $R_1$ and $R_2$ are alkyl groups, straight or branched, containing from 1 to about 30 carbon atoms and $R_3$ and $R_4$ are alkyl groups, straight or branched, containing from 1 to about 12 carbon atoms.

Compounds having the structure $$R_1-O\overset{O}{\underset{\|}{C}}-CH_2-CH_2-S-\overset{S}{\underset{\|}{C}}-\underset{\underset{R_3}{|}}{N}CH_2-CH_2-\underset{\underset{R_4}{|}}{N}-\overset{S}{\underset{\|}{C}}-$$
$$-S-CH_2-CH_2-\overset{O}{\underset{\|}{C}}O-R_2$$

are particularly useful in steel on bronze applications of which the compound in accordance with Example 4, dioctyl 6,9-diaza-6,9-dimethyl-4,11-dithia-5,10-dithiotetra decanoate, is a new composition of matter.

The following examples illustrate the alkyl beta-thiopropionic esters in accordance with the herein embodied invention and antiwear data showing their utility as lubricant improvers. It is understood, however, that the invention is not limited to the particular antiwear additives described, and that various modifications thereof can be employed as will be readily apparent to those of ordinary skill in the art.

EXAMPLE 1

Preparation of Ethyl beta-n-hexylthiopropionate $$CH_3(CH_2)_5-SCH_2CH_2\overset{O}{\underset{\|}{C}}O-CH_2CH_3$$

1-Hexanethiol (25.0 g; 0.21 moles) was mixed with sodium methoxide catalyst (0.5 g) and the mixture cooled to below room temperature. Ethyl acrylate (27.0 g; 0.21 moles) was added dropwise, the temperature of the reaction mix being kept below 30° C. by cooling in an icebath. When the addition of the ethyl acrylate was complete, the mixture was permitted to come to room temperature and mixing continued for 1 hour. The catalyst was removed by diluting the reaction mixture with diethylether and extracting with dilute hydrochloric acid. The ether solution was then placed on a rotary evaporator and the solvent removed with heat (hot water) and vacuum.

The following spectral properties confirm the structure shown above:
ir (infared) (CHCl$_3$) 5.80 $\mu$ $$(-\overset{O}{\underset{\|}{C}}-O-),$$

7.28 $\mu$ (CH$_2$—S—C); nmr (nuclear magnetic resonance) (CDCl$_3$) $\delta$ 0.7–1.7 (multiplet, 14.1 H, CH$_3$ beta to oxygen and CH$_3$(CH$_2$)$_4$ from hexyl group), $\delta$ 2.07–2.9 (complex multiplet, 6.0 H, CH$_2$ from hexyl alpha to sulfur and —CH$_2$CH$_2$— between sulfur and carbonyl), $\delta$ 4.1 (quartet, 1.9 H, CH$_2$ alpha to oxygen and CH$_3$)

Analysis: Calc. for C$_{11}$H$_{22}$O$_2$S: C 60.51%, H 10.16%, O 14.65%, S 14.68%.

Found: C 60.52%, H 10.09%, O 14.64%, S 14.70%.

EXAMPLE 2

Preparation of Ethyl beta-n-butylthiopropionate $$CH_3(CH_2)_3-SCH_2CH_2\overset{O}{\underset{\|}{C}}O-CH_2CH_3$$

Ethyl beta-n-butylthiopropionate was prepared according to the procedure of Example 1 using 1-butanethiol (14.75 g, 0.16 moles), ethyl acrylate (16.0 g; 0.16 moles) and sodium methoxide (0.5 g.) The following spectral properties confirm the structure shown above:
ir(CHCl$_3$) 5.80 $\mu$ $$(-\overset{O}{\underset{\|}{C}}-O-),$$

7.28$\mu$ (CH$_2$—S—C); nmr (CDCl$_3$) $\delta$ 0.7–1.7 (multiplet, 10.0 H, CH$_3$ beta to oxygen and CH$_3$CH$_2$CH$_2$— from butyl group) $\delta$ 2.3–2.9 (complex multiplet, 6.0 H, CH$_2$ from butyl alpha to sulfur and —CH$_2$CH$_2$— between sulfur and carbonyl), $\delta$ 4.1 (quartet, 1.9 H, CH$_2$ alpha to oxygen and CH$_3$).

EXAMPLE 3

Preparation of n-Octyl beta-n-butylthiopropionate $$CH_3(CH_2)_3-SCH_2CH_2\overset{O}{\underset{\|}{C}}O-(CH_2)_7CH_3$$

Ethyl beta-n-butylthiopropionate (10.0 g; 0.05 moles) was mixed with n-octyl alcohol (6.85 g; 0.05 moles) and hydrochloric acid (3.0 ml of 37% solution in H$_2$O) and heated to 90° for 48 hours, flushing the reaction vessel with nitrogen to remove the methyl alcohol as it was evolved.

The following spectral properties confirm the structure shown above:

ir (CHCl$_3$) 5.80 μ

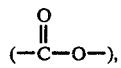

7.28 μ (CH$_2$—S—C); nmr (CDCl$_3$) δ 0.7–1.9 (multiplet; 22.1 H, CH$_3$(CH$_2$)$_6$ from octyl group and CH$_3$(CH$_2$)$_2$ from butyl group), δ 2.4–2.9 (complex multiplet, 6.1 H, CH$_2$ from butyl alpha to sulfur and —CH$_2$CH$_2$— between sulfur and carbonyl), δ 4.1 (triplet, 1.8 H, CH$_2$ alpha to oxygen).

EXAMPLE 4

Preparation of Dioctyl 6,9-diaza-6,9-dimethyl-4,11-dithia-5,10-dithiotetradecanoate

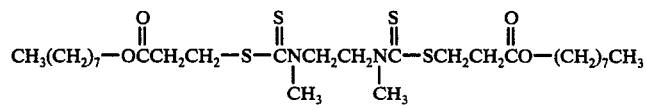

Carbon disulfide (27.1 g; 0.37 moles) was mixed with methyl acrylate (29.3 g; 0.34 moles) and cooled to below room temperature and sym-dimethyldiethylenediamine (15.0 g; 0.17 moles) was added dropwise. After the addition of the amine was complete, the mixture was permitted to come to room temperature and mixed for 18 hours. Then n-octyl alcohol (44.24 g; 0.34 moles) and hydrochloric acid (5.0 ml of 37% solution of H$_2$O were added, and the resultant solution was heated to 100° C for 116 hours, flushing the reaction vessel with nitrogen to remove the methyl alcohol as it was evolved. The following spectral properties confirm the structure shown above:

ir(CHCl$_3$) 5.78 μ

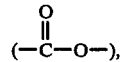

7.20 μ (CH$_2$—S—C); nmr (CDCl$_3$) δ 0.88 (triplet) and δ 1.3 (broad singlet, 29.8 H, CH$_3$(CH$_2$)$_6$ from two octyl groups), δ 2.5–2.9 (multiplet) δ 3.07 (sharp singlet) δ 3.3–3.7 (complex multiplet, total 18.2 H, respectively from 2—CH$_2$'s alpha to carbonyl and beta to sulfur, 2—CH$_3$'s on the nitrogen atoms, and 2—CH$_2$'s alpha to sulfur mixed with 2—CH$_2$'s alpha to oxygen), δ 3.9–4.4 (complex multiplet, 4.0 H, 2—CH$_2$'s between the two nitrogen atoms).

Analysis: Calc. for C$_{28}$H$_{52}$N$_2$S$_4$O$_4$: C 55.23%, H 8.61%, N 4.60%, O 10.51%.

Found: C 57.07%, H 9.56%, N 4.94%, O 10.21%.

Dioctyl, 6,9-diaza-6,9-dimethyl-4,11-dithia-5,10-dithiotetradecanoate to the best of applicants' knowledge and belief is a new compound having utility as an antiwear agent.

Testing Method:

Steel-on-Steel Wear

Additives were tested for antiwear activity using the Four Ball Wear Test, disclosed in U.S. Pat. No. 3,423,316. In general, in this test three steel balls of SAE 52100 steel are held in a ball cup. A fourth ball positioned on a rotatable vertical axis is brought into contact with the three balls and is rotated against them. The force with which the fourth is held against the three stationary balls may be varied according to a desired load. The test lubricant is added to the ball cup and acts as a lubricant for the rotation. At the end of the test, the steel balls are investigated for wear scar; the extent of scarring represents the effectiveness of the lubricant as an antiwear agent. Results are also reported as wear rates in volume of wear per unit sliding distance per kilogram load. The lower the wear rate, the more effective the lubricant as an antiwear agent. The base stock oil employed in accordance with the test results shown in Table 1 comprised a 150 SSU at 210° F solvent-refined paraffinic bright stock lubricating oil. In the data summarized in Table 1, all additives were tested at equimolar concentrations of 0.02 moles per kilogram of oil; the corresponding weight percentages are shown in the table. Standard conditions of 40 Kg. load, 600 rpm, and 30 minutes' test time were employed at 200° F.

Steel-on Bronze Wear

The method is identical to that given above for steel-on-steel wear with the following exceptions:

1. Three bronze discs (SAE-65) are substituted for the three stationary steel balls; and
2. Standard test conditions were 20 Kg. load, 3,000 rpm, and 20 minutes test time.

The test results are shown in Table II.

As will be apparent from the data of the following Tables, the lubricant compositions of the present invention exhibit highly improved antiwear properties both in steel-on-steel and steel-on-bronze applications, as evidenced by the comparative data therein with respect to wear scar diameter and wear rate.

While the present invention has been described with reference to preferred compositions and modifications thereof, it will be apparent to those skilled in the art that departure from the preferred embodiments can be effectively made and are within the scope of the specification.

Table I

| | Four Ball Wear Test Results - Steel-on-Steel | | | | |
|---|---|---|---|---|---|
| | 40 Kg. load, 600 rpm, 30 minutes | | | | |
| | | | | 200° F | |
| Ex. | Compound | Wt. % | Coeff. of Friction | Wear Scar Diameter mm | Wear Rate × 10$^{12}$ cc/cm-Kg. |
| — | Base Stock Only | — | 0.087 | 0.686 | 4.60 |
| 1 | CH$_3$(CH$_2$)$_5$—S—CH$_2$CH$_2$CO—CH$_2$CH$_3$ (O double bond) | 0.44 | 0.070 | 0.455 | 0.62 |

Table I-continued
Four Ball Wear Test Results - Steel-on-Steel
40 Kg. load, 600 rpm, 30 minutes

| | | | 200° F | | |
|---|---|---|---|---|---|
| Ex. | Compound | Wt. % | Coeff. of Friction | Wear Scar Diameter mm | Wear Rate × $10^{12}$ cc/cm-Kg. |
| 2 | $CH_3(CH_2)_3-S-CH_2CH_2\overset{\overset{O}{\|\|}}{C}O-CH_2CH_3$ | 0.38 | 0.080 | 0.432 | 0.53 |
| 3 | $CH_3(CH_2)_3-S-CH_2CH_2\overset{\overset{O}{\|\|}}{C}O-(CH_2)_7CH_3$ | 0.55 | 0.076 | 0.385 | 0.27 |
| 4 | $[CH_3(CH_2)_7-O\overset{\overset{O}{\|\|}}{C}-CH_2CH_2-S\overset{\overset{S}{\|\|}}{C}\underset{CH_3}{\overset{N-CH_2-}{\diagup}}]_2$ | 1.21 | 0.090 | 0.432 | 0.53 |

Table II
Four Ball Wear Test Results - Steel-on-Bronze
20 Kg. load, 3,000 rpm, 20 minutes

| | | | 175° F | | |
|---|---|---|---|---|---|
| Ex. | Compound | Wt. % | Coeff. of Friction | Wear Rate Diameter mm | Wear Rate × $10^{12}$ cc/cm-Kg. |
| — | Base Stock Only | — | 0.040 | 0.951 | 5.46 |
| 1 | $CH_3(CH_2)_5-S-CH_2CH_2\overset{\overset{O}{\|\|}}{C}O-CH_2CH_3$ | 0.44 | 0.037 | 0.919 | 4.59 |
| 2 | $CH_3(CH_2)_3-S-CH_2CH_2\overset{\overset{O}{\|\|}}{C}O-CH_2CH_3$ | 0.38 | 0.034 | 0.851 | 3.33 |
| 3 | $CH_3(CH_2)_3-S-CH_2CH_2\overset{\overset{O}{\|\|}}{C}O-(CH_2)_7CH_3$ | 0.55 | 0.038 | 0.817 | 2.80 |
| 4 | $[CH_3(CH_2)_7-O\overset{\overset{O}{\|\|}}{C}-CH_2CH_2-S\overset{\overset{S}{\|\|}}{C}\underset{CH_3}{\overset{N-CH_2-}{\diagup}}]_2$ | 1.21 | 0.036 | 0.741 | 1.85 |

We claim:

1. A lubricant composition containing a major amount of an oil of lubricating viscosity or a grease prepared therefrom and a minor amount sufficient to improve the antiwear properties thereof an alkyl-beta-thiopropionic acid ester having the structure

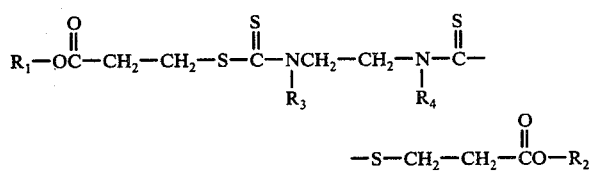

wherein $R_1$ and $R_2$ are alkyl groups straight or branched, containing from 1 to about 30 carbon atoms and $R_3$ and $R_4$ are alkyl groups, straight or branched, containing from 1 to about 12 carbon atoms.

2. The lubricant composition of claim 1 wherein the antiwear agent is dioctyl 6,9-diaza-6,9-dimethyl-4,11-dithia-5,10-dithiotetradecanoate.

3. The lubricant composition of claim 1 wherein the antiwear agent is present in an amount from about 0.05 to about 5% by weight of the total composition.

4. The lubricant composition of claim 3 wherein the antiwear agent is present in an amount from about 0.1 to about 2%, by weight.

5. The lubricant composition defined in claim 1 wherein said lubricant comprises an oil of lubricating viscosity.

6. The lubricant composition defined in claim 1 wherein said lubricant comprises a mineral oil.

7. The lubricant composition defined in claim 1 wherein said lubricant comprises a synthetic oil.

8. The lubricant composition defined in claim 1 wherein said lubricant comprises a hydraulic oil.

9. The lubricant composition defined in claim 1 wherein said lubricant comprises a transmission oil.

10. The lubricant composition defined in claim 1 wherein said lubricant comprises a grease.

11. A method of decreasing wear of bearing surfaces having at least two movable parts, wherein said bearing surfaces are steel or wherein one of said bearing surfaces is steel and another of said bearing surfaces is bronze, which comprises dispersing between said surfaces a lubricant composition characterized by a major amount of an oil of lubricating viscosity or a grease prepared therefrom and a minor amount sufficient to improve the antiwear properties thereof of an alkyl-beta-thiopropionic acid ester having the structure

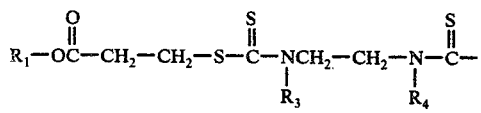

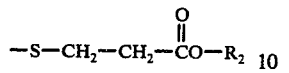

wherein $R_1$ and $R_2$ are alkyl groups, straight or branched, containing from 1 to about 30 carbon atoms and $R_3$ and $R_4$ are alkyl groups, straight or branched, containing from 1 to about 12 carbon atoms.

12. The method of claim 11 wherein the antiwear agent is dioctyl 6,9-diaza-6,9-dimethyl-4,11-dithia-5,10-dithiotetradecanoate.

13. The method of claim 11 wherein the antiwear agent is present in an amount from about 0.05 to about 5%, by weight of the total composition.

14. The method of claim 13 wherein the antiwear agent is present in an amount from about 0.1 to about 2%, by weight.

15. The method of claim 11 wherein said lubricant comprises a mineral oil.

16. The method of claim 11 wherein said lubricant comprises a synthetic oil.

17. The method of claim 11 wherein said lubricant comprises a grease.

18. Dioctyl 6,9-diaza-6,9-dimethyl-4,11-dithia-5,10-dithio tetradecanoate.